(12) United States Patent
Bohannon et al.

(10) Patent No.: US 7,458,942 B2
(45) Date of Patent: Dec. 2, 2008

(54) SYSTEMS AND METHODS FOR COLLECTING, TESTING AND TRANSPORTING LIQUID BIOLOGICAL SPECIMENS

(75) Inventors: Robert Bohannon, Chapel Hill, NC (US); Bud M. Owens, Greensboro, NC (US); Alan Morris, Burlington, NC (US); Glen Chapman, Graham, NC (US)

(73) Assignee: MedTox, St. Paul, MN (US)

( * ) Notice: Subject to any disclaimer, the term of this patent is extended or adjusted under 35 U.S.C. 154(b) by 159 days.

(21) Appl. No.: 10/948,083

(22) Filed: Sep. 22, 2004

(65) Prior Publication Data

US 2006/0064032 A1 Mar. 23, 2006

(51) Int. Cl.
*A61B 5/00* (2006.01)
*B65D 81/00* (2006.01)
*A61M 1/00* (2006.01)
*A61F 5/44* (2006.01)

(52) U.S. Cl. ............ 600/584; 600/573; 600/574; 600/575; 604/318; 604/319; 604/326; 604/329

(58) Field of Classification Search .......... 600/584, 600/573, 574, 575, 576; 604/318, 319, 326, 604/329
See application file for complete search history.

(56) References Cited

U.S. PATENT DOCUMENTS

| | | | | |
|---|---|---|---|---|
| 3,224,434 A | * | 12/1965 | Molomut et al. | 600/562 |
| 5,119,830 A | * | 6/1992 | Davis | 600/584 |
| 5,403,551 A | * | 4/1995 | Galloway et al. | 422/58 |
| 5,429,804 A | * | 7/1995 | Sayles | 422/58 |
| 5,501,837 A | * | 3/1996 | Sayles | 422/58 |
| 5,595,187 A | * | 1/1997 | Davis | 600/584 |
| 5,662,631 A | * | 9/1997 | Marx | 604/352 |
| 5,797,855 A | * | 8/1998 | Hazard et al. | 600/573 |
| 5,800,779 A | * | 9/1998 | Johnson | 422/58 |
| 5,897,840 A | * | 4/1999 | Owens et al. | 422/102 |
| 5,916,815 A | * | 6/1999 | Lappe | 436/92 |
| 5,976,469 A | * | 11/1999 | Davis | 422/102 |
| 5,976,895 A | * | 11/1999 | Cipkowski | 436/518 |
| 5,985,675 A | * | 11/1999 | Charm et al. | 436/514 |
| 6,168,758 B1 | * | 1/2001 | Forsberg et al. | 422/61 |
| 6,322,499 B1 | * | 11/2001 | Evans et al. | 600/212 |
| 6,403,383 B1 | * | 6/2002 | Casterlin et al. | 436/518 |
| 6,488,669 B1 | * | 12/2002 | Sagona et al. | 604/318 |
| 6,517,780 B1 | * | 2/2003 | Cortelazzo | 422/102 |
| 6,589,749 B1 | * | 7/2003 | Guirguis | 435/7.2 |
| 6,627,152 B1 | * | 9/2003 | Wong | 422/58 |
| 6,669,908 B2 | * | 12/2003 | Weyker et al. | 422/58 |

(Continued)

*Primary Examiner*—Max Hindenburg
*Assistant Examiner*—Jeffrey G Hoekstra
(74) *Attorney, Agent, or Firm*—Townsend and Townsend and Crew LLP

(57) ABSTRACT

A collection system for collecting, testing and transporting liquid biological specimens that limits exposure of a tester to the liquid sample and keeps the collected samples pristine even after exposing some of the sample to test strips. The system includes a collection body for receiving and holding a liquid sample, a lid that is coupled to the body, and a test strip housing. The lid includes a transfer conduit while the test strip housing includes an opening defined within the test strip housing. The transfer conduit and the opening are aligned when the test strip housing is coupled to the lid. When the system is moved or tilted, some of the liquid sample moves through the transfer conduit and the opening into the test strip housing.

54 Claims, 7 Drawing Sheets

U.S. PATENT DOCUMENTS

| | | | |
|---|---|---|---|
| 6,786,179 B2 * | 9/2004 | Ver Hage | 119/72 |
| 6,818,452 B2 * | 11/2004 | Wong | 436/169 |
| 6,837,858 B2 * | 1/2005 | Cunningham et al. | 600/573 |
| 2003/0133847 A1 * | 7/2003 | Hagen et al. | 422/104 |
| 2004/0133128 A1 * | 7/2004 | Guan et al. | 600/584 |
| 2004/0176704 A1 * | 9/2004 | Stevens et al. | 600/584 |
| 2005/0227370 A1 * | 10/2005 | Ramel et al. | 436/514 |
| 2005/0251064 A1 * | 11/2005 | Roe | 600/583 |
| 2006/0178600 A1 * | 8/2006 | Kennedy et al. | 600/584 |

* cited by examiner

SYSTEMS AND METHODS FOR COLLECTING, TESTING AND TRANSPORTING LIQUID BIOLOGICAL SPECIMENS

CROSS-REFERENCES TO RELATED APPLICATIONS

NOT APPLICABLE

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK.

NOT APPLICABLE

BACKGROUND OF THE INVENTION

1. Field of the Invention

The present invention relates to systems and methods for collecting, testing and transporting liquid biological specimens of bodily fluids, such as urine, and more particularly, to a collection system that includes a collection body for collecting a liquid sample and a test strip cassette coupled to a lid over the collection body, wherein the test strip cassette is in fluid communication with the collection body.

2. Description of the Prior Art

Testing of bodily fluid specimens, such as urine, has become well-known in today's society. Test strips are generally used. Unfortunately, such testing frequently exposes the tester to contact with the bodily fluid. Compounding this problem, there is often a need, as in hospital emergency rooms or the like, to carry out testing of bodily fluids quickly, thus increasing the likelihood of exposure of the tester.

Many attempts have been made to provide collection apparatuses and systems that limit exposure of the tester to the liquid sample. Unfortunately, many of the proposed systems are complicated and require training, often extensive, of testing personnel to precisely carry out the procedures.

Additionally, with many of the prior art devices, the test strips are placed into the original urine sample thereby potentially contaminating the sample with reagents and bio-burdens from the test strips. Thus, the original sample may not be retested thereby preventing confirmation testing.

Thus, there is a need for a device to collect liquid samples, particularly urine specimens, and perform rapid testing (drugs of abuse, DOA, or DAU) in a one-step process without the tester being exposed to the urine sample. Preferably, such a device would be inexpensive and have the flexibility to alter the tests being run. Such a device would allow incorporation of an adulteration strip and temperature sensing strip. The test strips within the cartridge housing should be capable of being scanned and photographed for analysis, if needed. Preferably, the collected sample remains pristine and allows for confirmation testing even after providing a sample to the test strips.

SUMMARY OF THE INVENTION

Broadly, the present invention provides a collection body for receiving and holding a liquid sample. A lid is provided that is coupled to the body to maintain the liquid sample therein. Structure is provided on top of the lid for receiving a test strip housing or cassette. The lid further includes a transfer conduit defined therein for allowing a small amount of the liquid sample to transfer to a test strip housing coupled to the lid. Furthermore, the test strip housing broadly comprises a test strip receiving area, including at least one test strip reservoir, an opening defined within the test strip housing for alignment with the transfer conduit, and housing mating structure around the opening for mating with the structure on the lid.

In accordance with one aspect of the present invention, the test strip housing comprises a vent located adjacent the test strip receiving area.

In accordance with another aspect of the present invention, the vent is defined within a cover over the test strip receiving area and is located at a position relative to the opening whereby during use of the system, fluid level of liquid sample within the test strip receiving area is defined by positioning of the vent.

In accordance with a further aspect of the present invention, the cover over the test strip receiving area is substantially clear.

In accordance with another aspect of the present invention, the test strip housing comprises a trough adjacent the at least one test strip reservoir.

In accordance with a further aspect of the present invention, a manifold pad is positioned within the trough.

In accordance with another aspect of the present invention, a test strip is positioned within the at least one test strip reservoir.

In accordance with yet another aspect of the present invention, the transfer conduit is positioned approximately one-half inch from an edge of the lid.

In accordance with a further aspect of the present invention, the transfer conduit is defined within a substantially conical protrusion.

In accordance with yet another aspect of the present invention, the test strip housing receiving structure comprises a partially circular protrusion that defines two lips and the housing mating structure comprises a partially circular receiving portion that includes tabs that engage the lips.

In accordance with another aspect of the present invention, the transfer conduit comprises an inlet and an outlet, wherein the inlet is larger than the outlet.

In accordance with a further aspect of the present invention, the test strip receiving area comprises a plurality of test strip reservoirs.

In accordance with yet another aspect of the present invention, a test strip is positioned within some of the test strip reservoirs and at least one adulteration strip is positioned within a test strip reservoir.

In accordance with yet another aspect of the present invention, the lid and the collection body are coupled together with cooperating threads.

In accordance with a further aspect of the present invention, the test strip housing receiving structure comprises a partially circular protrusion that comprises two lips while the housing mating structure comprises a partially circular receiving portion that includes tabs that engage the lips.

In accordance with another aspect of the present invention, the housing mating structure and the test strip housing receiving structure are coupled together with a one-quarter turn that causes the tabs to engage the lips.

In accordance with a further aspect of the present invention, the lid includes an arch defined within its periphery and the test strip housing comprises an arch defined within its periphery with the test strip housing arch portion extending beyond the lid arch portion when the test strip housing is coupled to the lid.

In accordance with another aspect of the present invention, the housing mating structure and the test strip housing receiving structure are coupled together with a snap-on connection.

In accordance with a further aspect of the present invention, the housing mating structure and the test strip housing receiving structure are coupled together with a slide-on connection.

In accordance with another aspect of the present invention, the housing mating structure and the test strip housing receiving structure are coupled together with a magnetic connection.

In accordance with further aspect of the present invention, the body comprises a marker to indicate a minimum amount for a liquid sample.

In accordance with another aspect of the present invention, the body comprises at least one side protrusion on an outer surface that defines a corresponding indentation on an inner surface.

In accordance with yet another aspect of the present invention, the body comprises at least three side protrusions on an outer surface that define corresponding indentations on an inner surface.

In accordance with a further aspect of the present invention, the coupling structure and the mating structure comprise cooperating magnetic components.

In accordance with another aspect of the present invention, the coupling structure and the mating structure comprise cooperating snaps.

The present invention also provides a method of collecting and testing a liquid sample where the method comprises providing a liquid sample within a collection body. A lid is coupled to the collection body, where the lid includes a transfer conduit defined therein. A test strip housing is coupled to the lid, where the test strip housing includes an opening defined therein that is aligned with the transfer conduit. The test strip housing further includes a test strip receiving area. At least one test strip is provided within the test strip receiving area. The method further comprises moving the collection body so that liquid sample moves through the transfer conduit and the opening, and engages the at least one test strip.

In accordance with another aspect of the present invention, the method further comprises providing a vent located at a position relative to the opening whereby during use of the system, fluid level of liquid sample within the test strip receiving area is defined by positioning of the vent.

In accordance with a further aspect of the present invention, the collection body is moved until an edge of the test strip housing engages a support surface and the method further comprises allowing the test strip housing edge to rest on the support surface.

In accordance with another aspect of the present invention, the test strip housing edge rests on the support surface in a range of three to five minutes.

In accordance with yet another aspect of the present invention, the test strip housing edge rests on the support surface in a range of one to 15 seconds.

In accordance with a further aspect of the present invention, the method further comprises moving the edge of the test strip housing away from the support surface and removing the test strip housing.

In accordance with yet another aspect of the present invention, the method further comprises sealing the opening in the lid after removing the test strip housing for subsequent shipment and/or storage.

In accordance with yet another aspect of the present invention, the method further comprises photocopying the test strip housing after removing the test strip housing.

In accordance with another aspect of the present invention, the method further comprises reading the test strip housing with an electronic reader after removing the test strip housing.

In accordance with another aspect of the present invention, the method further comprises moving the edge of the test strip housing away from the support surface and reading the test strip housing while the test strip housing is coupled to the lid.

In accordance with yet another aspect of the present invention, the test strip housing is read visually.

In accordance with yet another aspect of the present invention, the test strip housing is read electronically.

Thus, the present invention provides a system for collecting and testing liquid samples that includes a collection body and a removable strip cassette housing mounted onto the top of a custom lid, whereby a urine sample collected can be applied to the cassette housing through aligned small orifices. The interface of the lid and the housing is achieved with a conically shaped cone fashioned to reduce the amount of urine on the interface when the cassette is removed and the body is upright by making the opening towards the urine specimen in the collection body larger that the opening at the crest or peak of the conical connection. Preferably, a small orifice or vent is provided in the cassette housing that allows the sample to enter the opening of the cassette and rise to the level where the vent is located. This prevents the sample from rising above that level due to the air pocket formed above the vent hole, thereby eliminating flooding of the test strips.

Other features and advantages of the present invention will be apparent upon review of the following detailed description of preferred exemplary embodiments.

DETAILED DESCRIPTION OF THE INVENTION

Figure 1:
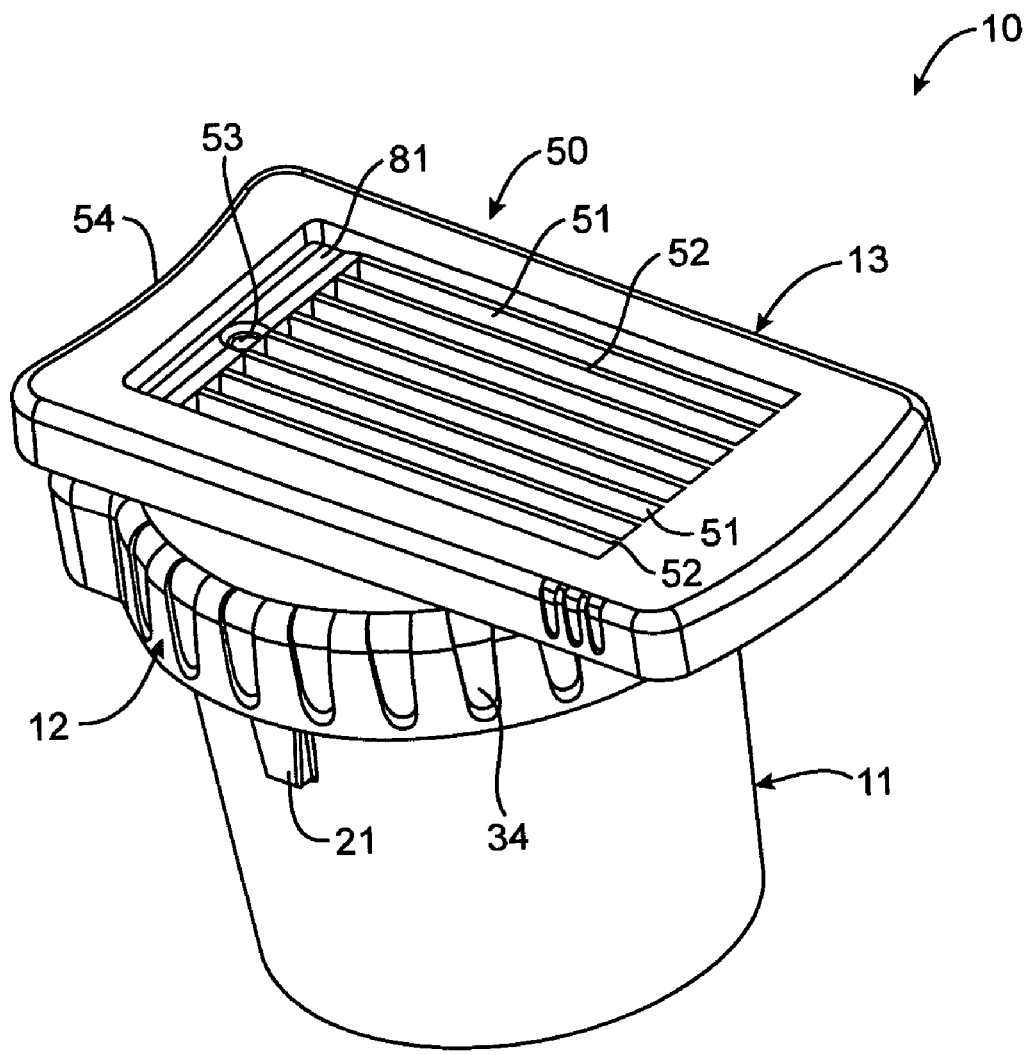
FIG. 1 is a perspective view of a collection system in accordance with the present invention.

FIG. 1 illustrates a test device system 10 in accordance with the present invention. Preferably, the system includes a cup or collection body 11, a lid 12 and a test strip cassette or housing 13. Briefly, the system is used to a collect liquid sample in the cup, hold the sample in the cup with the lid and transfer a portion of the liquid sample through the lid into the test strip housing as will be more fully explained herein.

Figure 2:
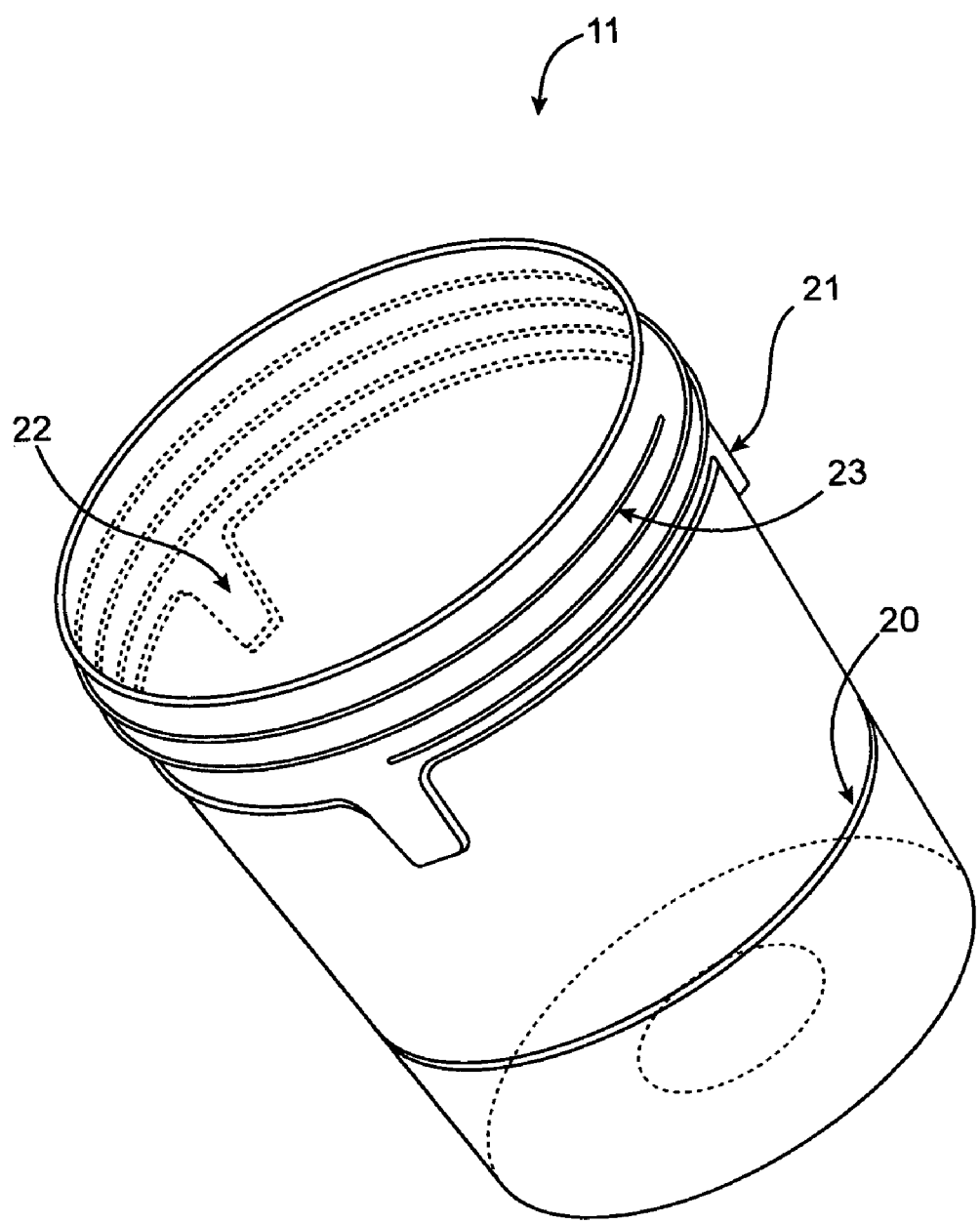
FIG. 2 is a perspective view of a collection body for use with the present invention.

Turning to FIG. 2, the cup is generally circular in shape and preferably includes some type of marker 20 to indicate whether enough liquid sample for confirmation testing is present. Additionally, this marker will help indicate whether enough sample is in the cup to use for rapid in-field testing. Furthermore, preferably the cup includes protrusions 21 on the outer surface that define corresponding indentations 22 on the inner surface. The protrusions and indentations facilitate nesting of empty cups. In a preferred embodiment there are three such protrusions and indentations. Threads 23 are preferably provided along a top periphery of the cup to allow for a leak proof coupling of the lid thereto.

Figure 5:
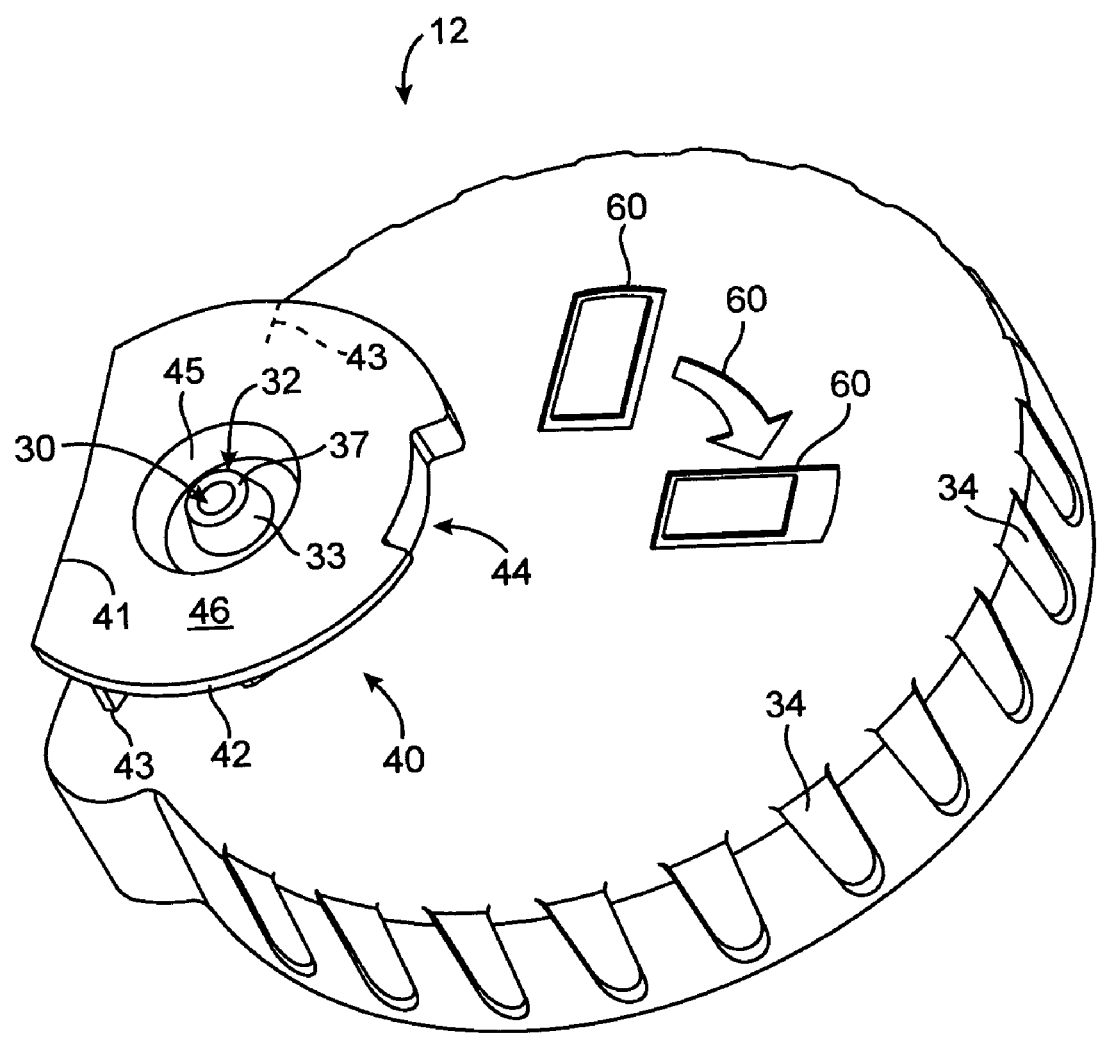
FIG. 5 is a top perspective view of a lid for use with the present invention.
Figure 6:
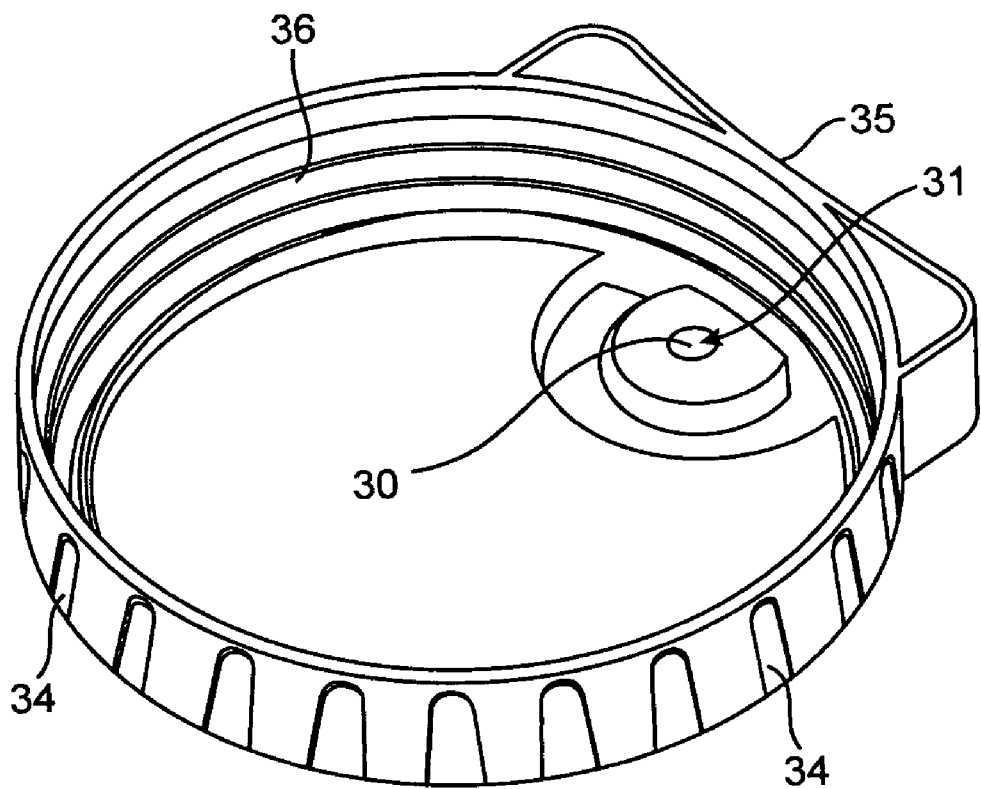
FIG. 6 is a bottom perspective view of the lid illustrated in FIG. 5.
Figure 7:
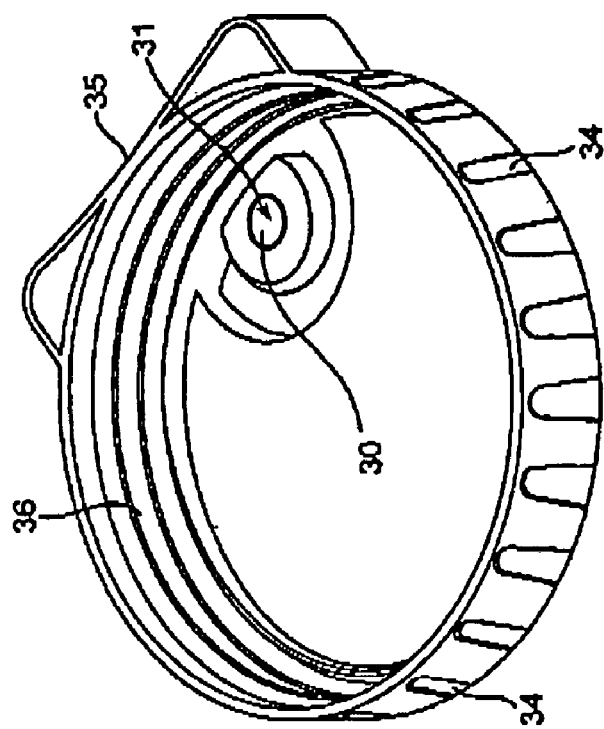
FIG. 7 is a top and bottom perspective view of the lid, showing an alternative embodiment wherein the inlet to the transfer conduit (31) is larger than the outlet (32).
Figure 7:
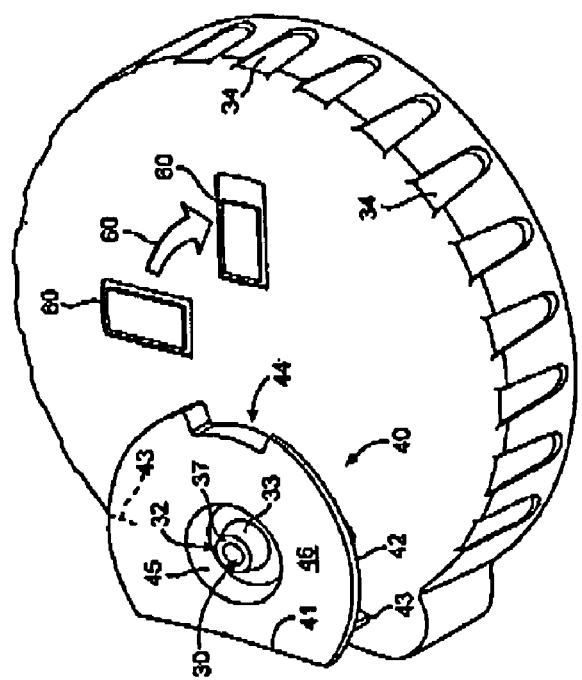

With reference to FIGS. 5 and 6, it can be seen that the lid includes a transfer conduit 30. Preferably, inlet 31 of the transfer conduit is slightly larger than outlet 32 of the transfer conduit. Additionally, as may be seen in FIG. 5, a top portion 33 of the transfer conduit is preferably conical shaped.

Around the periphery of the lid, indentations 34 are preferably provided to allow for a better grip by a user. Additionally, an arch 35 is preferably defined for allowing the lid, when coupled to a cup, to engage a machine for confirmation testing. Around an interior portion of the periphery of the lid, threads 36 are provided for cooperation with threads 23 on the cup to thereby allow leak proof coupling of the lid to the cup. Other methods of coupling may be used as long as the lid and cup are sealed to prevent leaking. Examples of other coupling techniques include magnetic components and snaps.

Around the upper portion of the transfer conduit and on a top portion of the lid, structure 40 is provided for receiving a test strip housing. As may be seen, preferably the structure is a partial semicircle, with a flat portion 41 thereof aligning with arch 35. The upper portion of the structure defines a lip 42. Under the lip are two stop tabs 43 that cooperate with structure on the test strip housing. Furthermore, opposite the flat portion, an indentation 44 is provided that also cooperates with the test strip housing as will be further described herein. Depression 45 is defined within structure and surrounds upper portion 33 of the transfer conduit. As may be seen in FIG. 5, top surface 37 of the transfer conduit is substantially flush with top surface 46 of structure 40.

Figure 3:
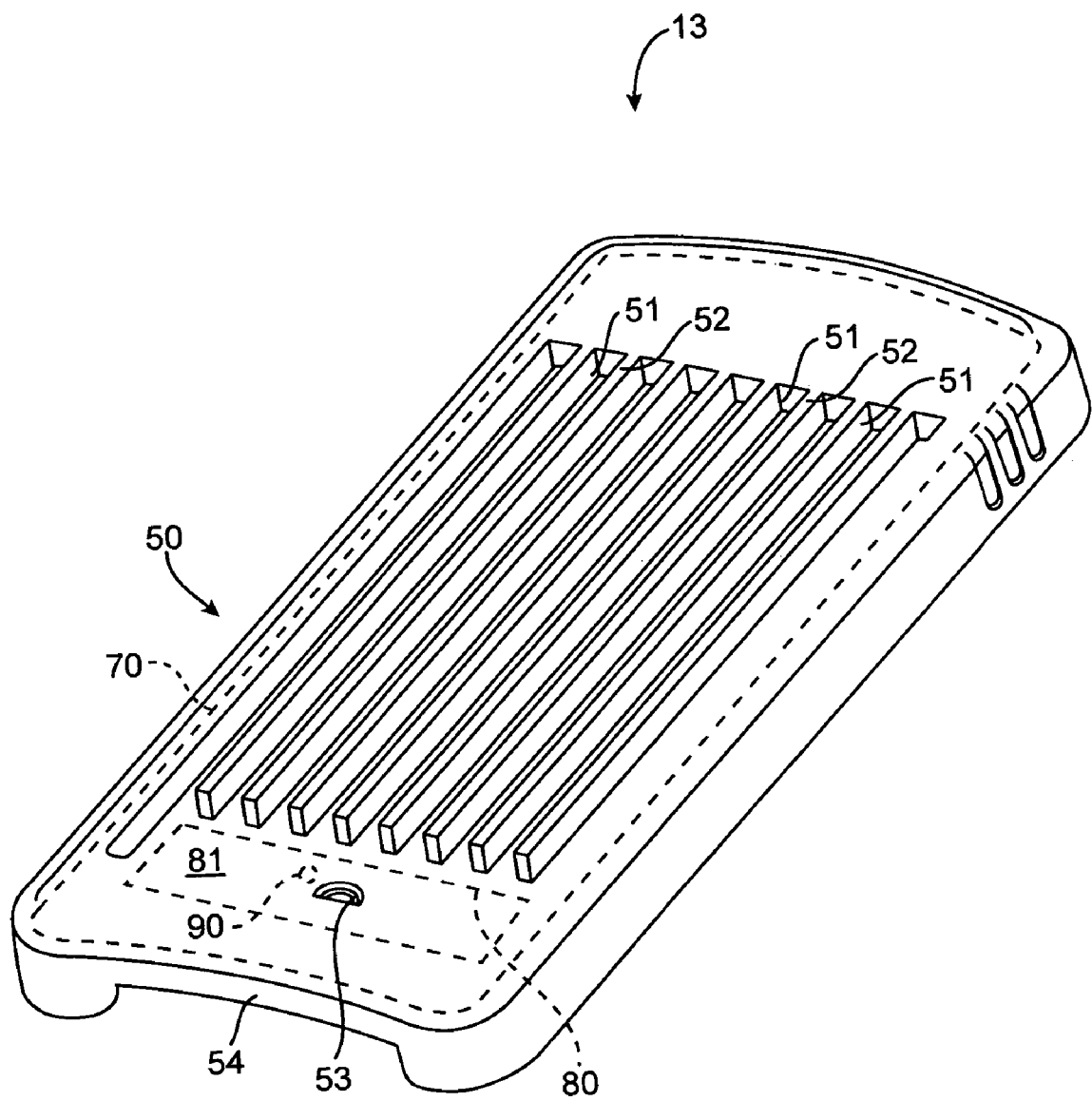
FIG. 3 is a top perspective view of a test strip housing for use with the present invention.
Figure 4:
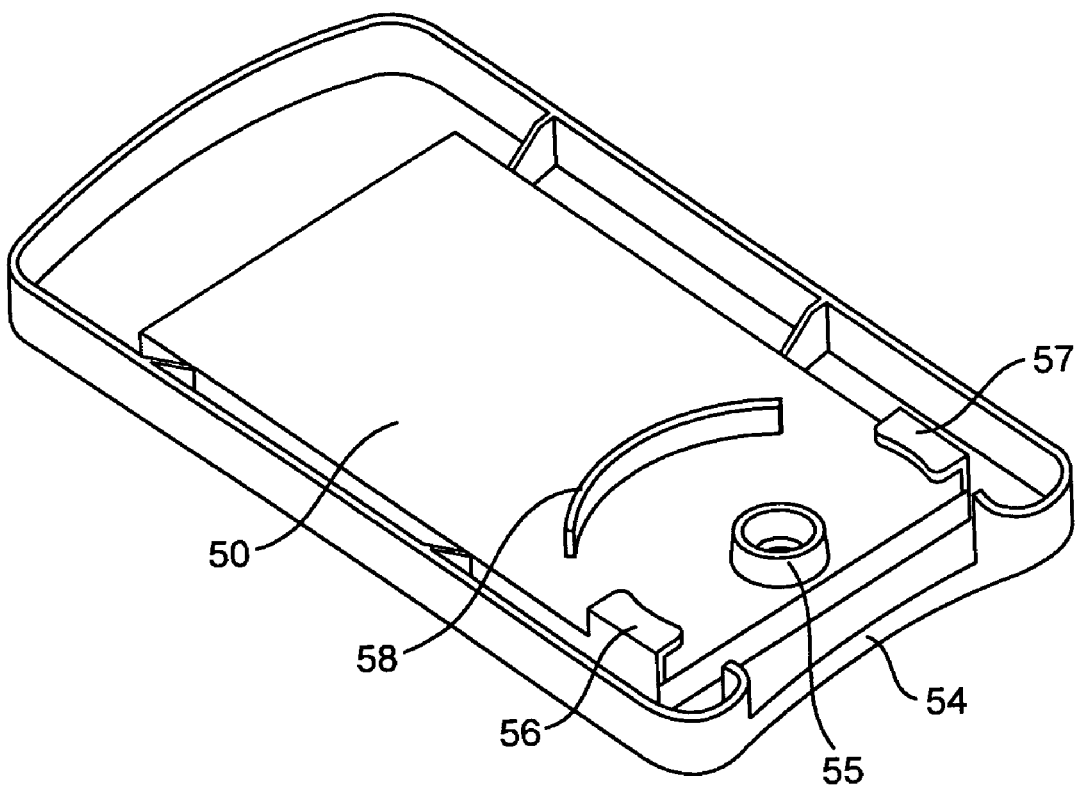
FIG. 4 is a bottom perspective view of the test strip housing illustrated in FIG. 3.

Turning to FIGS. 3 and 4, it can be seen that the test strip housing includes a test strip receiving area 50. Preferably the test strip receiving area is divided into a plurality of test strip reservoirs 51 by a plurality of dividers 52. Test strips and adulteration pads may be placed within the test strip reservoirs.

Adjacent the test strip reservoirs is an opening 53 defined adjacent the test strip receiving area. Preferably, this opening is defined within the bottom of the test strip housing. At this proximal end of the test strip housing, an arch 54 is defined within a periphery of the test strip housing.

With reference to FIG. 4, it may be seen that a ring protrusion 55 is preferably provided around the opening. Around this ring protrusion, mating structure is provided that cooperates with the receiving structure on the lid. In a preferred embodiment, the mating structure includes two opposing tabs 56, 57 and preferably includes a semicircular barrier 58 for added stability.

Thus, when coupling the test strip housing to lid, the housing is placed such that ring protrusion 55 extends over conical-shaped portion 33 of the transfer conduit. One tab is placed adjacent indentation 44 while the second tab is placed adjacent flat portion 41. By turning the cassette one quarter turn, the tabs move under the lip and engage the stop tabs. Thus, the tabs cannot be pulled up past the lip and therefore, the test strip housing is now coupled to the lid. As may be seen in FIG. 5, preferably markings 60 are provided on the lid to indicate how to couple the test strip housing to the lid.

The ring protrusion now surrounds the conical shape portion of the transfer conduit within depression 45 and thus, prevents liquid from leaking at this point when liquid moves through the liquid conduit and through the opening in the test strip housing. Furthermore, top surface 37 of transfer conduit 30 tightly engages the bottom of the test strip housing with the openings aligned, thereby preventing leaking of the liquid sample.

Additionally, arch 54 is aligned with arch 35. Arch 54 extends slightly beyond arch 35.

Those skilled in the art will understand that other arrangements may be used to couple the test strip housing to the lid, such as, a snap-on arrangement, a slide-on arrangement, magnetic components and adhesives. Any such arrangement needs to provide a good seal between the transfer conduit and the test strip housing so that liquid does not leak and should also allow for removal of the test strip housing.

A cover or overlay 70 is provided over the test strip receiving area. This cover is permanently attached to the test strip housing in a leak proof manner. Preferably, the cover is clear or substantially clear to allow viewing or partial viewing of at least some strips within the test strips reservoirs. This allows for visual examination, photocopying, and scanning of test strips within the test strip area. Alternatively, the entire test strip housing may be clear or at least a portion over the test strip receiving area so that the housing may be made in as few a components as possible if desired.

A manifold pad 80 may be provided along a trough 81 defined over opening 53 to help promote rapid spread of the liquid sample along one or more test strips and adulteration pads contained within the test strip reservoirs.

In a preferred embodiment, a vent 90 is provided within the overlay. Preferably, the vent is about 1 mm in diameter and may be circular, rectangular, or any other desired shape. Additionally, in a preferred embodiment the vent is located adjacent to opening 53. In this preferred embodiment, the vent prevents the liquid sample from rising above its location due to an air pocket formed above the vent within the test strip housing when the system is placed on its side. Those skilled in the art will understand that the vent may be placed in other locations within the test strip housing. A purpose of the vent is to prevent flooding or over saturation of the test strips and any adulterations strips.

An example of dimensions for the cup includes a top diameter of 67.5 mm wide, a bottom diameter of 59.4 mm wide, and a height of 84 mm. An example of dimensions for the lid includes an inside diameter of approximately 68 mm. An example of dimensions for the test strip housing includes a width of approximately 55 mm and length of approximately 103 mm. Preferably, the components are made of a fairly rigid material such as, for example, plastic.

Accordingly, the test device system is operated by providing a liquid sample, into the cup. When testing a urine sample, this is generally done by providing the patient with a cup who then voids into the cup (urinates), and attaching a lid to the cup. A testing person opens a sealed cassette or test strip housing and attaches it onto the lid with a one-quarter locking motion. Preferably, the lid has a place to provide a patient ID number on it as does the cassette.

The tester then sets the cup on its side against arch 54 defined within the test strip housing. This allows the urine sample to flow into the test strip housing thereby starting the test. Once the test is started, the tester can either set the cup upright after a few seconds and wait three to five minutes to read the test strips, or has the option of leaving the cup on its side for three to five minutes and reading the strips while the cup is on its side.

Thus, as the liquid sample flows into the test strip housing, it is absorbed by pad 80 (if used) within the trough and absorbed by the test strips and any adulteration pads within the test strip reservoirs. The sample moves along the strips due to the capillary action created by the absorbency of the strips and pads. The liquid sample does not flow above the vent (if a vent is included) due to the air pocket formed above the vent. The liquid sample does not flow back into the cup due to the sizing and placement of the openings as well as the absorbency of the strips and pads. Thus, since liquid sample that has been exposed to the strips does not flow back into the cup, the sample remaining within the cup is not exposed to reagents and bio-burdens from the test strips and adulteration pads. Thus, the remaining sample in the cup is pristine and may be used for confirmation testing.

Once the exposure of the strips to the liquid sample is complete, the results on the strips may be read while the housing is attached to a lid, either visually or in some electronic manner. The housing may also be removed from the lid at which time the strips may be read, once again either visually or electronically, and maybe photocopied. The tester may remove the cassette to photocopy the results, place the strip into an electronic reader (BioDot, Camag, digital camera or other reader), or may simply dispose of the cassette. Thus, it is desirable that the overlay have at least some clear portions that allow for viewing of the strips.

Once the test strip housing is removed, if confirmation testing or any other type of further testing is desired, opening 53 is sealed with a permanent tag that goes over conical shaped portion 33 of the transfer conduit. By locating this conical portion approximately half an inch from the edge of the lid, the cup and lid may be read by an automated reader or robot. Arch 35 is placed against the robot and the robot is able to pierce the permanent tag due to the location of the transfer conduit, thereby allowing the machine or robot to access the pristine liquid sample remaining within the cup. This allows for further testing of the liquid sample. The permanent tag preferably surrounds the conical portion within depression 45. Preferably, a chain or custody security label is placed over the entire lid/cup arrangement.

Accordingly, the present invention provides a system that allows for rapid testing in the field while allowing for a pristine portion of the liquid sample to remain for confirmation testing or further testing back at a laboratory. Furthermore, due to the interfacing of the cassette strip housing with the lid, a tester is minimally exposed to any of the liquid sample as the one way flow provided by the inventive system eliminates liquid sample from appearing externally even after removal of the test strip housing.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A collection system for collecting a liquid sample, the collection system comprising:
    a body for receiving and holding the liquid sample, the body including a coupling structure defined at a top portion of the body for receiving a lid;
    the lid including a mating structure for mating with the coupling structure, the lid further comprising a test strip housing receiving structure on a top portion of the lid, and around a transfer conduit defined therein; and
    a test strip housing removably coupled to the lid through the test strip housing receiving structure, the test strip housing comprising a test strip receiving area, outside of the lid, having at least one test strip reservoir, and further comprising an opening defined within the test strip housing for alignment with the transfer conduit within the lid; and
    surrounding the opening, a housing mating structure for mating with the test strip housing receiving structure on the top portion of the lid, thereby coupling the test strip housing to the lid.

2. A collection system in accordance with claim 1, further comprising a vent located adjacent the test strip receiving area.

3. A collection system in accordance with claim 2 wherein the vent is defined within a cover over the test strip receiving area and is located at a position relative to the opening whereby during use of the system, fluid level of liquid sample within the test strip receiving area is defined by positioning of the vent.

4. A collection system in accordance with claim 3 wherein the cover over the test strip receiving area is clear.

5. A collection system in accordance with claim 1, wherein the test strip housing comprises a trough adjacent the at least one test strip reservoir.

6. A collection system in accordance with claim 5 wherein a manifold pad is positioned within the trough.

7. A collection system in accordance with claim 1, wherein a test strip is positioned within the at least one test strip reservoir.

8. A collection system in accordance with claim 1 wherein the transfer conduit is positioned approximately one-half inch from an edge of the lid.

9. A collection system in accordance with claim 1 wherein the transfer conduit is defined within a conical protrusion that extends such that a top of the conical protrusion is substantially flush with a top surface of the test strip housing receiving structure.

10. A collection system in accordance with claim 9 wherein the transfer conduit comprises an inlet and an outlet, and wherein the inlet is larger than the outlet.

11. A collection system in accordance with claim 1, wherein the test strip receiving area comprises a plurality of test strip reservoirs.

12. A collection system in accordance with claim 11, wherein a test strip is positioned within at least one of the test strip reservoirs.

13. A collection system in accordance with claim 2, wherein the transfer conduit is defined within a conical protrusion that extends such that a top of the conical protrusion is substantially flush with a top surface of the test strip housing receiving structure.

14. A collection system in accordance with claim 13 wherein the transfer conduit comprises an inlet and an outlet, and wherein the inlet is larger than the outlet.

15. A collection system in accordance with claim 1 wherein the coupling structure and the mating structure comprise cooperating threads.

16. A collection system in accordance with claim 1, wherein the test strip housing receiving structure comprises a partially circular protrusion that defines two lips and the housing mating structure comprises a partially circular receiving portion that includes tabs that engage the lips.

17. A collection system in accordance with claim 16 wherein the transfer conduit is defined within a conical protrusion that extends such that a top of the conical protrusion is flush with a top surface of the test strip housing receiving structure.

18. A collection system in accordance with claim 17 wherein the housing mating structure further comprises a ring protrusion that at least partially surrounds the conical protrusion.

19. A collection system in accordance with claim 18 wherein the transfer conduit comprises an inlet and an outlet, and wherein the inlet is larger than the outlet.

20. A collection system in accordance with claim 1, wherein the lid includes a first arch portion defined with its periphery and the test strip housing comprises a second arch portion defined within its periphery, the second arch portion extending beyond the first arch portion when the test strip housing is coupled to the lid.

21. A collection system in accordance with claim 16 wherein the housing mating structure and the test strip housing receiving structure are coupled together with a one-quarter turn that causes the tabs to engage the lips.

22. A collection system in accordance with claim 1, wherein the housing mating structure and the test strip housing receiving structure are coupled together with a snap-on connection.

23. A collection system in accordance with claim 1, wherein the housing mating structure and the test strip housing receiving structure are coupled together with a slide-on connection.

24. A collection system in accordance with claim 1, wherein the housing mating structure and the test strip housing receiving structure are coupled together with a magnetic connection.

25. A collection system in accordance with claim 1 wherein the body comprises a marker to indicate a minimum amount for a liquid sample.

26. A collection system in accordance with claim 1 wherein the body comprises at least one side protrusion on an outer surface that defines a corresponding indentation on an inner surface.

27. A collection system in accordance with claim 1 wherein the body comprises at least three side protrusions on an outer surface that define corresponding indentations on an inner surface.

28. A collection system in accordance with claim 1 wherein the coupling structure and the mating structure comprise cooperating magnetic components.

29. A collection system in accordance with claim 1 wherein the coupling structure and the mating structure comprise cooperating snaps.

30. A collection system for collecting a liquid sample, the collection system comprising:
  a body for receiving and holding the liquid sample, the body including a coupling structure defined at a top portion of the body for receiving a lid;
  the lid comprising: a mating structure for mating with the coupling structure, a transfer conduit defined within a conical protrusion, having an inlet, located on the bottom of the lid and an outlet, located on the top of the lid, wherein the inlet is larger than the outlet; a test strip housing receiving structure on a top portion of the lid, the test strip housing receiving structure further comprising a depression surrounding an upper portion of the transfer conduit defined therein; and
  a test strip housing removably coupled to the test strip housing receiving structure on the top portion of the lid, the test strip housing comprising a test strip receiving area comprising at least one test strip reservoir; and
  further comprising an opening defined within the test strip housing for alignment with the transfer conduit within the lid; and
  surrounding the opening, a housing mating structure for mating with the test strip housing receiving structure on the top portion of the lid, thereby coupling the test strip housing to the lid.

31. A collection system in accordance with claim 30 further comprising a vent located adjacent the test strip receiving area.

32. A collection system in accordance with claim 31 wherein the vent is defined within a cover over the test strip receiving area and is located at a position relative to the opening whereby during use of the system, fluid level of liquid sample within the test strip receiving area is defined by positioning of the vent.

33. A collection system in accordance with claim 32 wherein the cover over the test strip receiving area is clear.

34. A collection system in accordance with claim 30 wherein the test strip housing comprises a trough adjacent the at least one test strip reservoir.

35. A collection system in accordance with claim 34 wherein a manifold pad is positioned within the trough.

36. A collection system in accordance with claim 30 wherein a test strip is positioned within at least one test strip reservoir.

37. A collection system in accordance with claim 30 wherein the transfer conduit is positioned approximately one-half inch from an edge of the lid.

38. A collection system in accordance with claim 30 wherein the transfer conduit is defined within a conical protrusion that extends such that a top of the conical protrusion is flush with a top surface of the test strip housing receiving structure.

39. A collection system in accordance with claim 38 wherein the housing mating structure further comprises a ring protrusion that at least partially surrounds the conical protrusion.

40. A collection system in accordance with claim 39 wherein the test strip housing receiving structure comprises a partially circular protrusion that defines two lips and the housing mating structure comprises a partially circular receiving portion that includes tabs that engage the lips.

41. A collection system in accordance with claim 40 wherein the housing mating structure and the test strip housing receiving structure are coupled together with a one-quarter turn that causes the tabs to engage the lips.

42. A collection system in accordance with claim 30 wherein the coupling structure and the mating structure comprise cooperating threads.

43. A collection system in accordance with claim 30 wherein the lid comprises a first arch portion defined with its periphery and the test strip housing comprises a second arch portion defined within its periphery, the second arch portion extending beyond the first arch portion when the test strip housing is coupled to the lid.

44. A collection system in accordance with claim 30 wherein the housing mating structure and the test strip housing receiving structure are coupled together with a snap-on connection.

45. A collection system in accordance with claim 30 wherein the housing mating structure and the test strip housing receiving structure are coupled together with a slide-on connection.

46. A collection system in accordance with claim 30 wherein the housing mating structure and the test strip housing receiving structure are coupled together with a magnetic connection.

47. A collection system in accordance with claim 30 wherein the body comprises a marker to indicate a minimum amount for a liquid sample.

48. A collection system in accordance with claim 30 wherein the body comprises at least one side protrusion on an outer surface that defines a corresponding indentation on an inner surface.

49. A collection system in accordance with claim 30, wherein the body comprises at least three side protrusions on an outer surface that define corresponding indentations on an inner surface.

50. A collection system in accordance with claim 30 wherein the coupling structure and the mating structure comprise cooperating magnetic components.

51. A collection system in accordance with claim 30 wherein the coupling structure and the mating structure comprise cooperating snaps.

52. A collection system in accordance with claim 11 wherein an adulteration strip is positioned within at least one of the test strip reservoirs.

53. A collection system in accordance with claim 30, wherein an adulteration strip is positioned within at least one test strip reservoir.

54. A collection system for collecting a liquid sample, the collection system comprising
  (i) a body for receiving and holding the liquid sample,
  (ii) a lid comprising a test strip housing receiving structure on top of the lid, and
  (iii) a test strip housing removably coupled to the test strip housing receiving structure on top of the lid, wherein:
  the body further comprising a coupling structure defined at a top portion of the body for receiving the lid
  the lid further comprising a mating structure for mating with the coupling structure at the top portion of the body, and a test strip housing receiving structure on a top portion of the lid around a transfer conduit defined therein; and
  the test strip housing further comprising an opening defined within the test strip housing for alignment with the transfer conduit and a test strip receiving area having at least one test strip reservoir,
  wherein the test strip housing is coupled to the test strip receiving structure on the top portion of the lid through a coupling structure selected from the group consisting of: a one-quarter turn connection, a snap-on connection, a slide-on connection, and a magnetic component connection, thereby coupling the test strip housing to the lid.

* * * * *